United States Patent [19]
Taylor, Jr.

[11] 3,999,121
[45] Dec. 21, 1976

[54] WELL CASING CORROSION METER

[75] Inventor: John M. Taylor, Jr., Tulsa, Okla.

[73] Assignee: Standard Oil Company (Indiana), Chicago, Ill.

[22] Filed: Aug. 11, 1975

[21] Appl. No.: 603,845

[52] U.S. Cl. .................. 324/65 CR; 23/253 C; 204/195 C
[51] Int. Cl.[2] .................................. G01R 27/02
[58] Field of Search ........... 324/65 CR; 204/1 C, 204/195 C; 23/230 C, 253 C

[56] References Cited
UNITED STATES PATENTS

| | | | |
|---|---|---|---|
| 3,406,101 | 10/1968 | Kilpatrick | 324/65 CR |
| 3,684,679 | 8/1972 | Smith et al. | 204/195 C |

*Primary Examiner*—Stanley T. Krawczewicz
*Attorney, Agent, or Firm*—Albert C. Metrailer; Arthur McIlroy

[57] ABSTRACT

Apparatus for making a surface measurement of well casing external corrosion current including a voltmeter, a variable current source, a reference electrode, and a ground electrode. Current is coupled to the well casing to ground circuit by means of the ground electrode to cause a preselected small, less than 0.02 volt, potential change in the well casing relative to the reference electrode. The voltmeter is used to measure the applied current level which is, for a fixed casing potential change, proportional to well casing corrosion current.

9 Claims, 9 Drawing Figures

WELL CASING CORROSION METER

BACKGROUND OF THE INVENTION

This invention relates to apparatus for measuring external well casing corrosion current and, more particularly, to apparatus for making a surface measurement of external well casing corrosion current.

Well casing corrosion has been recognized as a major source of failures in producing wells. Both external electrolytic and galvanic corrosion occur to some extent in practically all wells. If no protection is provided, the corrosion eventually perforates the well casing and extensive repairs and costly time delays are required to restore the well to producing capacity. Many corrosion-preventing measures such as electrically insulating pipeline connections from wellheads have become standard field operating procedures. The cathodic protection of well casing has also become a standard procedure and has proved effective in stopping the corrosion of well casings. Cathodic protection has typically been provided either by the use of buried sacrificial anodes made of, for example, magnesium electrically connected to the well casing, or by means of rectifiers which convert standard 60-cycle alternating current to a direct current which is coupled to a ground electrode for conduction to the well casing.

With any method of cathodic protection, the initial capital investment and continuing operation and maintenance costs are related to the level of cathodic current which must be supplied to a well casing. It is therefore desirable to supply the minimum current which will effectively prevent external casing corrosion. It has been recognized that the minimum corrosion preventing or protective current is related to the total corrosion current flowing from the well casing to the earth. Efforts to minimize the cost of cathodic protection have, therefore, centered on efforts to measure the well casing corrosion current.

Two basic methods of measuring well casing corrosion current have been employed. The first, a downhole logging technique, is considered to be the most reliable but is the most expensive in terms of equipment and shutdown time of the well required to perform the test. In this method a logging tool having two sets of contact blades spaced vertically apart, typically 15 to 25 feet, is first lowered down the wellbore and then raised in steps equal to or greater than the blade spacing. The tool is stopped and the blades are forced into contact with the inside surface of the well casing. The voltage differential between the two sets of contact blades is then measured and used together with the presumed value of casing resistance to determine the current flowing in the section of well casing. When the casing currents are plotted versus position of the well casing, locations of decreasing current in the casing metal indicate that the current is leaving the well casing and therefore corrosion is occurring. The downhole log may also be repeated after cathodic protection current is applied to the well casing to determine what minimum level of cathodic current is required to eliminate all anodic areas of the well casing.

The second basic method of measuring external well casing corrosion current is known as the E-log I surface measurement technique. In this method the potential of the well casing relative to a reference electrode is measured after a cathodic current has been applied to the casing for some time period. The current is increased in steps to a current range far exceeding the corrosion current and the protective current levels. The voltage measurements are plotted on a linear scale versus the current levels on a logarithmic scale from which the name E-log I plot is derived. It is believed by some that the E-log I curves should always have at least one straight line portion commonly referred to as the Tafel region of the curve. In field use this Tafel region is typically extrapolated back to the native state well casing potential and the corresponding current level is assumed to be the corrosion current level. Other theories hold that the current at the break point between the curved portion of the curve and the linear portion represents the corrosion current level. Various other theories of the meaning and use of the E-log I plots indicate that the plot actually has no linear portion, or possibly should have two linear portions. This confusion as to the meaning of E-log I plots, coupled with the empirical data showing inconsistencies between surface E-log I measurements and downhole logging techniques, has resulted in a general lack of confidence in the technique by oil well operators.

It has been theorized and experimentally confirmed in laboratories that the E-log I plot has a linear portion occuring very close to the native state potential of the well casing. A publication illustrating this theory and typical laboratory testing is "A Method for Determining Corrosion Rates from Linear Polarization Data" by Milton Stern, published in *Corrosion*, Vol. 14, p. 440T, in September 1958. The experimental work indicated an inverse relationship between actual corrosion current and the polarization resistance measured as the change in potential of a corroding electrode specimen divided by the applied current for a potential change in the range of 10 mv. For various reasons it has been assumed that this correlation has no application in the field of oil well casing corrosion. A measurement of this polarization resistance is necessarily a surface measurement and it has long been known that data from the older surface measurement technique, E-log I plots, are not reproducible and are inconsistent with downhole logs. It has also been assumed that any attempt to impress a small voltage change on the order of 10 my upon a well casing by surface contact only would be futile and would have no effect at any appreciable depth. This assumption is based on downhole logs which indicate that cathodic protection currents tend to be concentrated in the top few thousand feet of well casings.

Therefore, an object of the present invention is to provide an improved apparatus for measuring well casing corrosion current.

Another object of present invention is to provide an apparatus for measuring well casing corrosion current using surface contacts only.

Another object of the present invention is to provide a simple and inexpensive means for measuring well casing corrosion current.

Another object of the present invention is to provide means for making a rapid and reproducible measurement of well casing corrosion current.

These and other objects of the present invention are achieved by providing apparatus comprising a voltage measuring means, a variable current source, a ground electrode, a reference electrode, and means for contacting a well casing at ground level. The current source provides a stable current to the well casing to earth circuit to cause and maintain a change in well casing potential relative to the reference electrode of, for example, 10 mv. The voltage sensing means is then connected to detect a voltage proportional to the current generated by the current source. For a fixed well casing potential change, the applied current is proportional to corrosion current.

The invention will be more fully understood by reading the following detailed description of the preferred embodiment with reference to the attached drawings wherein:

FIG. 1 is a schematic illustration of the test connections between a well casing corrosion meter according to the present invention and a well casing, and FIGS. 2 and 3 are, together, a complete schematic diagram of the well casing corrosion meter of FIG. 1.

DESCRIPTION OF PREFERRED EMBODIMENT

Figure 1:
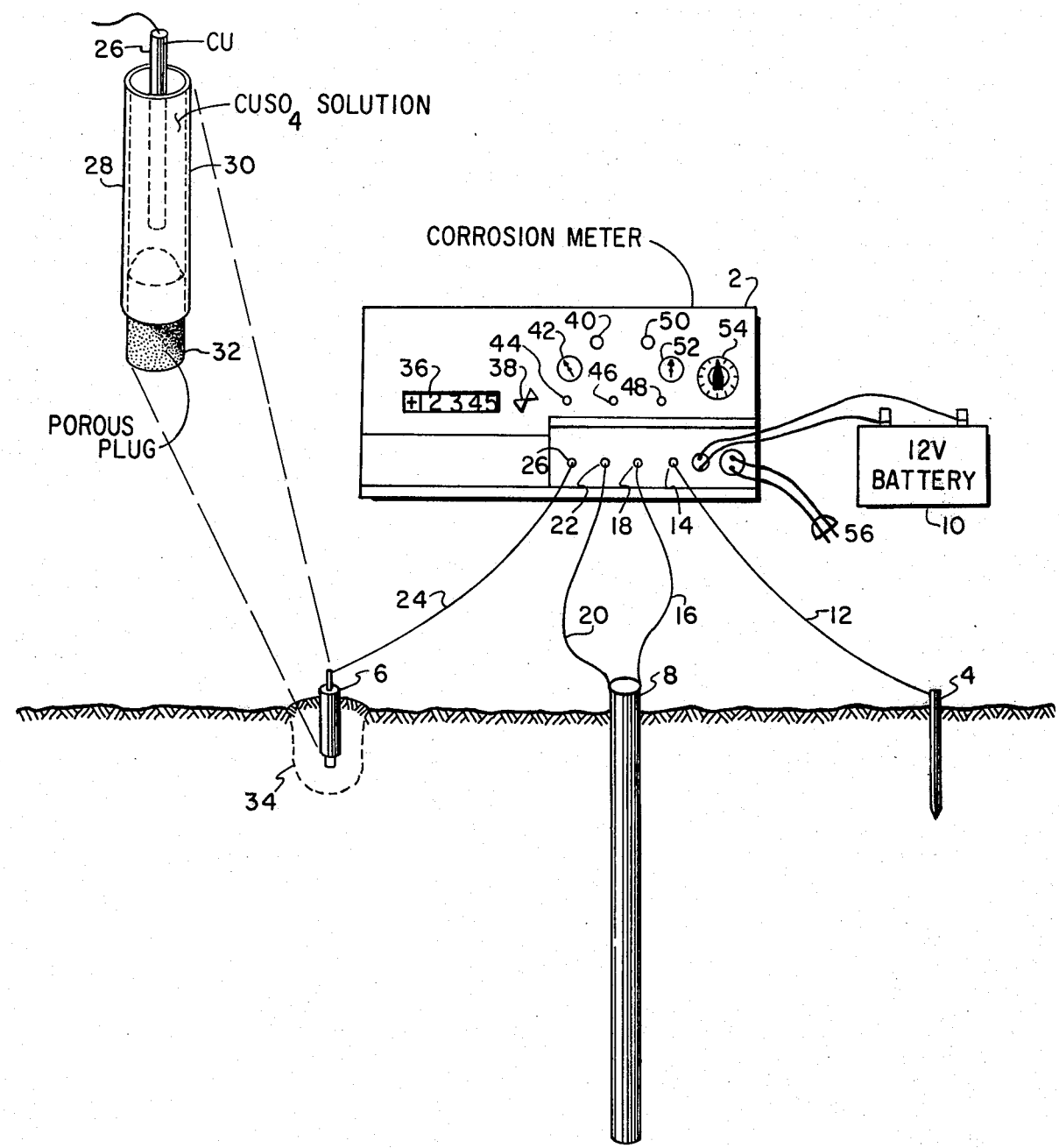

FIG. 1 illustrates the interconnection of a well casing corrosion meter 2 according to the present invention, a ground electrode 4, a reference electrode 6, and a well casing 8 for measurement of the corrosion current flowing from well casing 8. Additionally, there is illustrated in FIG. 1 a 12-volt lead acid storage battery 10 which is connected to the corrosion meter 2 to provide a test current to well casing 8. The meter 2 is coupled to ground electrode 4 by means of a single conductor cable 12, connected to a terminal 14 on the face of meter 2. Electrode 4 is typically a piece of iron such as, for example, a length of 1-in. diameter pipe which is driven into the ground at a distance of approximately 300 feet from the well casing 8. More elaborate ground electrodes such as, for example, other nearby well casings may also be used as electrode 4. A second single conductor cable 16 is connected from a terminal 18 on meter 2 to the head of well casing 8. Cables 12 and 16 are part of a test current loop in which, for example, meter 2 supplies current from terminal 14 through cable 12 to the ground electrode 4. Ground electrode 4 conducts current to the earth and it flows to well casing 8 and is then returned to meter 2 through cable 16 and terminal 18.

A third single conductor cable 20 is connected from a terminal 22 on meter 2 to the head of well casing 8. A fourth single conductor cable 24 is coupled from a terminal 26 on meter 2 to the reference electrode 6. Reference electrode 6 comprises a solid copper rod 26 centered in an insulating tube 28 which is filled with a saturated copper sulfate solution 30. The bottom portion of insulating tube 28 is closed by a porous plug 32 which may be, for example, soft wood or porous ceramic material. Reference electrode 6 is placed in contact with the earth by being positioned in a hole indicated by dotted line 34 which is backfilled with loose soil and then flooded with water. Reference electrode 6 is spaced from well casing 8 at a distance substantially equal to the space between ground electrode 4 and casing 8, but directly on the opposite side of well casing 8. This arrangement prevents current from meter 2 from interfering with the voltage reading taken between casing 8 and reference electrode 6. Cables 20 and 24 couple voltages from casing 8 and reference electrode 6 to meter 2 for detection of voltage changes caused by currents coupled from ground electrode 4 to well casing 8.

Corrosion meter 2 includes a digital voltmeter having a digital readout 36, and a voltage range switch 38. Meter 2 also includes a function switch 40 for switching the inputs to the digital voltmeter to detect the condition of the internal batteries and the external battery 10, to null the meter 36, to read well casing potential relative to reference electrode 6, and to read current supplied to well casing 8. Meter 2 includes a null potentiometer 42 and a null polarity switch 44. A switch 46 allows the direction of current supplied from terminal 14 to be reversed. A switch 48 controls power to meter 2. A switch 50 controls the range of current which may be supplied to well casing 8, while a potentiometer 52 allows precise adjustment of this test current. Meter 2 additionally includes a timer 54 which must be activated before test current will be supplied to well casing 8 and allows a precise determination of the time period of each test which is run. An AC power cord 56 is also provided with the meter 2 to allow recharging of internal batteries in voltmeter 36 when meter 2 is not being used.

Figure 2:
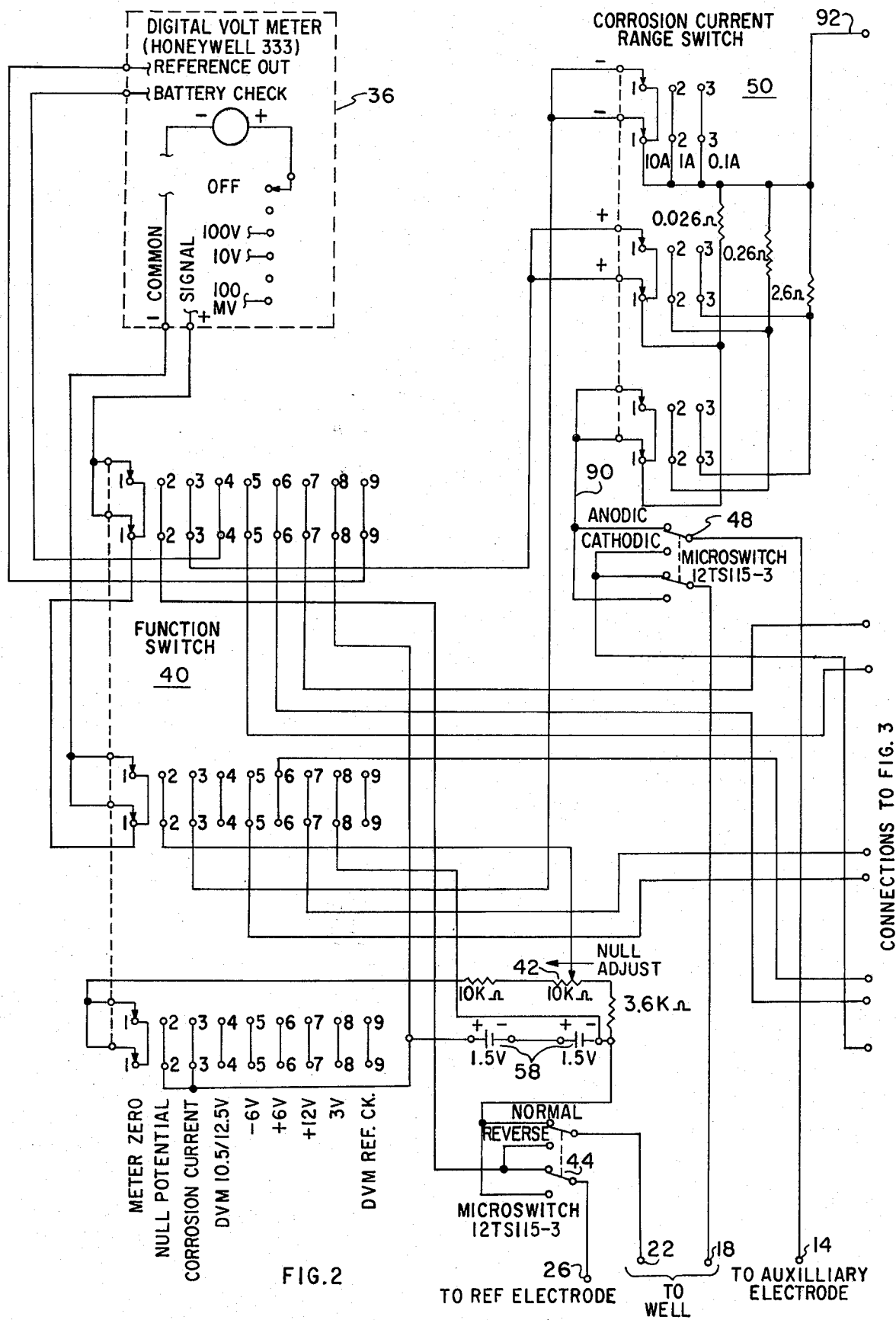
Figure 3:
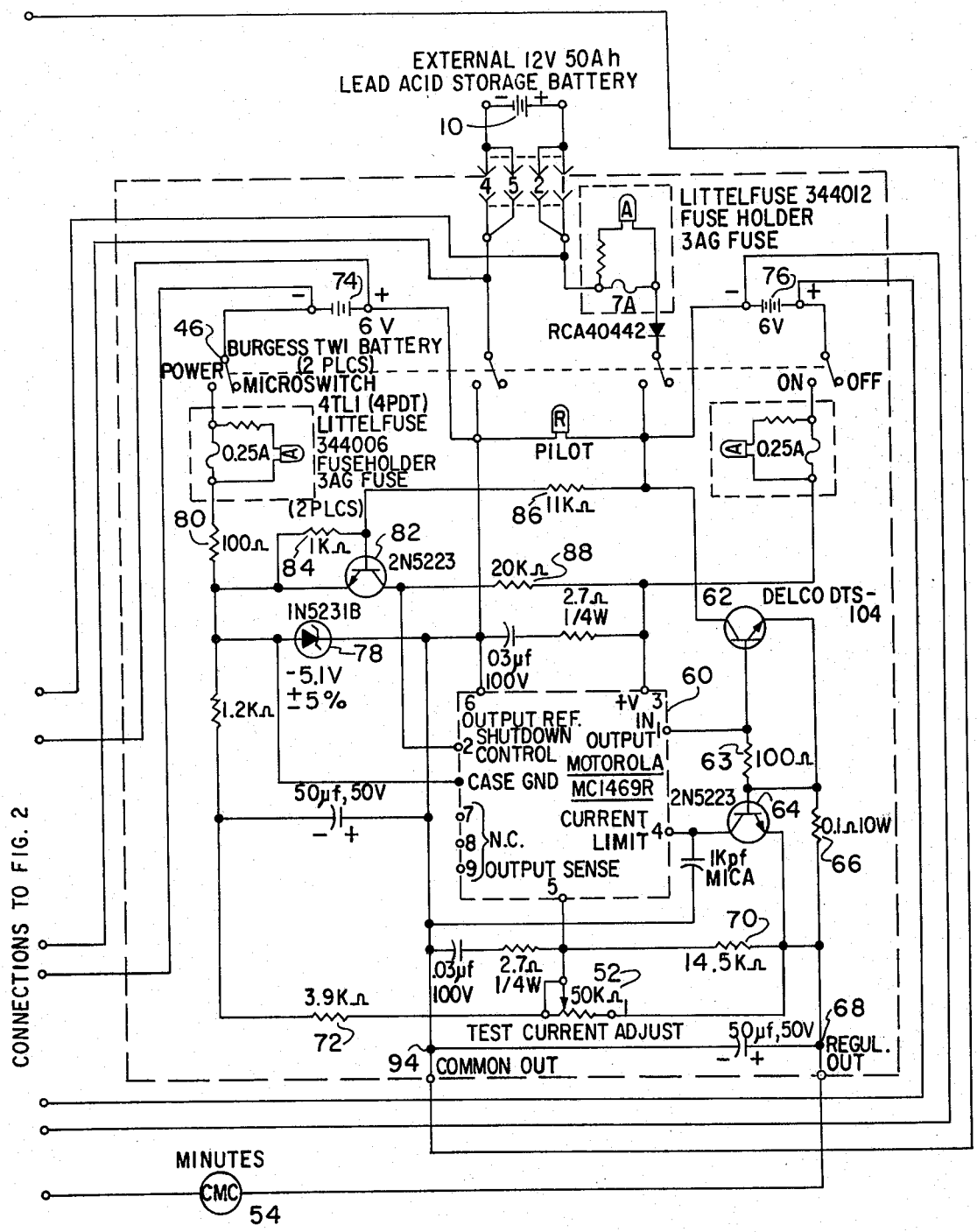

FIGS. 2 and 3, taken together, comprise an entire schematic diagram of the corrosion meter 2 of FIG. 1. The same reference numerals are used to designate parts corresponding to those illustrated in FIG. 1. Corrosion meter 2 includes a voltage-sensing element, which in the preferred embodiment is a Honeywell Corporation Model 333 digital voltmeter. The signal and common inputs of voltmeter 36 are connected to two poles of a three-pole nine-position switch which is the function switch 40 of FIG. 1. As illustrated in FIG. 2, function switch 40 is actually a six-pole nine-position switch in which the poles are connected in pairs to reduce switch-contact resistance and insure contact for each switch pole should one contact become inoperative. The nine switch positions are labeled in FIG. 2 according to the function performed by voltmeter 36 in each of the positions.

The third pole of function switch 40 is used to connect a null adjusting circuit in switch positions 2 and 3, which are the null potential and corrosion-current measuring positions, respectively. In switch positions 2 and 3, a pair of 1½ volt batteries 58 are connected across a three-resistor voltage divider in which null-adjust potentiometer 42 is the center resistor. In switch position 2, the first two poles of function switch 40 couple a voltage which comprises the well-to-reference electrode voltage in series with the null-adjustment voltage appearing on the wiper of null-adjust potentiometer 42 to the signal input of voltmeter 36. While function switch 40 is in position 2 and cables 20 and 24 of FIG. 1 are coupled to the well casing and reference electrode, respectively, null-adjust potentiometer 42 is adjusted for a zero voltage reading on voltmeter 36. The polarity of the null-adjusting voltage may be reversed, if necessary, by double-pole double-throw 44.

While function switch 40 is in position 2 monitoring the well casing-to-reference electrode potential, circuitry within corrosion meter 2 comprising essentially that illustrated in FIG. 3 is used to supply a regulated current to the well casing through the auxiliary electrode terminal 14. The current generator illustrated in FIG. 3 is basically a well regulated voltage source having an output voltage controlled by the test-current adjustment potentiometer 52 of FIGS. 1 and 3. This current generator comprises an integrated-circuit voltage regulator 60 and peripheral circuitry for providing limits on output current, shutdown for low battery voltages, and power amplification of the output regulated voltage. In this preferred embodiment, integrated-circuit regulator 60 is a standard Motorola Semiconductor Corporation Part No. MC1469R. The voltage output of regulator 60 is coupled to the base of a power transistor 62, which may be, for example, a Delco type DTS-104. The voltage output of circuit 60 is also coupled through a resistor 63 to the junction of the emitter of transistor 62 and the base of a current-limiting transistor 64. Current flowing from the emitter of transistor 62 flows through a resistor 66 coupled from the base to the emitter of transistor 64. Resistor 66 is a 0.1-ohm resistor and limits the output current to 7 amps, since, above this current level, transistor 64 will turn on and its collector will draw current from a current-limit input of circuit 60. Resistor 66 and the emitter of transistor 64 are also coupled to a regulator voltage output 68. The regulated voltage of output 68 is also coupled to a resistive voltage divider comprising resistor 70 and 72, and the test-current adjustment potentiometer 52. The wiper of potentiometer 52 is connected to an output voltage sense input of circuit 60 and thereby controls the regulator output voltage appearing at output 68.

Circuit 60 receives power from a pair of 6-volt batteries 74 and 76, contained within corrosion meter 2, and also from the external storage battery 10, which in the preferred embodiment is a lead-acid storage battery such as that used by the vehicle in which corrosion meter 2 is transported to a test site. The voltage generated by battery 74 also appears across a series circuit comprising a zener diode 78 and a resistor 80. Zener diode 78 is coupled from an output reference input to the case ground input of circuit 60 to provide a stable reference voltage. A transistor 82 and its base circuit resistors 84 and 86 and collector-load resistor 88 are coupled to batteries 19, 74, and 76 to detect a low-voltage condition in batteries 10 and 74. When the voltage of batteries 10 and 74 is too low, the voltage appearing across resistor 84 is no longer sufficient to maintain transistor 82 in the on-state. The collector of transistor 82 is coupled to the shutdown control input of circuit 60 so that, when it turns off, current flowing resistor 88 is coupled to the shutdown-control input to turn off the output of circuit 60.

Current flowing from the regulated voltage output 68 passes through the timer 54, when it has been set, to the current-direction switch 48. Switch 48 controls the direction in which the supplied current is coupled through the auxiliary electrode 4 to well casing 8 circuit. After passing through the auxiliary electrode to well casing circuit, the current is coupled through a lead 90 to the third wiper of a three-pole three-position corrosion current range switch 50. Switch 50 couples the current through one of three resistors which convert the test current to a voltage which is coupled through function switch 40 to the voltmeter 36 to provide an output reading of test current. From switch 50, the test current passes through a lead 92 back to a common output terminal 94 of the current-generating circuitry.

Before a corrosion-current test measurement is made, the switch positions 1 and 4 through 9 of function switch 40 are used to check the operation of digital voltmeter 36 and the condition of the batteries used to power corrosion meter 2. In function-switch position 1, the signal and common inputs to digital voltmeter 36 are shorted together, and, if a zero voltage reading is not obtained, an internal control in voltmeter 36 is adjusted to return the meter reading to the zero position. In function-switch position 4, the output voltage of a rechargeable battery pack built into voltmeter 36 is coupled to the voltmeter inputs and a reading of at least 10.5 volts is required for proper voltmeter operation. In function-switch position 5, the output of battery 74 of FIG. 3 is coupled to the inputs of voltmeter 36, and, if a reading below 5 volts results, battery 74 must be replaced. In function-switch position 6, the output of battery 76 is coupled to the inputs of voltmeter 36, and, if a reading below 5 volts results, battery 76 must be replaced. Function-switch position 7 couples the output voltage of external 12-volt battery 10 to the input of voltmeter 36, if it has been connected to the corrosion meter 2. In function-switch position 8, the output voltage of the two 1½ volt batteries 58 of FIG. 2 is coupled to the input of voltmeter 36 to check the condition of these batteries. In function-switch position 9, a reference-output voltage generated by voltmeter 36 is coupled to the input of voltmeter 36 and, with the voltmeter range switch in the 100-volt position, should generate a 10.00-volt reading. If this 10-volt reading is not obtained, an adjustment of an internal full-scale adjustment control within voltmeter 36 returns the reading to 10.00 volts.

After having verified the proper adjustments of voltmeter 36 and the condition of the batteries which supply power to corrosion meter 2, a corrosion-current reading may be made. If it has not been done previously, the 12-volt storage battery is connected to corrosion meter 2. Cables 12, 16, 20, and 24 are connected between the corrosion meter 2 and the ground electrode and well casing electrode as illustrated in FIGS. 1. Function switch 40 is then placed in position 2 and null-adjustment potentiometer 42 is adjusted to obtain a zero reading on voltmeter 36 when its range switch is in the 100 mv position. Null-potential reverse switch 44 is left in its normal position if a standard reference electrode, such as the copper/copper sulfate electrode 6 of preferred embodiment is used.

Having obtained a zero well casing to reference electrode reading on voltmeter 36, corrosion current range switch 50 is placed in the 1-ampere position, power switch 46 is turned on, and timer 54 is set for 15 minutes. Test-current adjustment potentiometer 52 is then quickly adjusted to obtain a 10-mv reading on digital voltmeter 36. A period of typically from five to ten minutes is required for the linear polarization of the well casing to stabilize and, during this period, the well casing to reference electrode potential will drift slowly. The test current must, therefore, be adjusted periodically during this time to maintain the 10 mv change. After the initial test current setting, the function switch is turned to position 3 to obtain a reading of the test current being supplied to the well casing. Corrosion-current range switch 50 is then switched to the position which gives the largest number of significant figures in the readout without exceeding the voltmeter range. After having set the corrosion-current range switch 50 to its optimum position, function switch 40 is returned to null-potential position 2 and the test-current potentiometer 52 is readjusted to maintain the 10 mv reading on voltmeter 36. Since the current generator of FIG. 3 is essentially a highly regulated voltage source, any change made in corrosion-current range switch 50 causes some change in the current supplied to the well casing, and therefore some change in the well casing to reference electrode voltage reading on voltmeter 36. This change, together with the normal drift occurring during the first part of the test cycle requires the readjustment of test current potentiometer 52. After the well casing to reference electrode potential has stabilized at 10 mv and just before the timer 54 has reached the end of its timing cycle, function switch 40 is returned to the corrosion current position 3 and a reading is taken from voltmeter 36 which indicates the corrosion current of well casing 8. In this embodiment the decimal point appearing in the voltage readout of voltmeter 36 is disregarded and the actual current being read is determined by observing the position of corrosion current range switch 50.

When timer 54 cuts off and while function switch 40 is still in position 3, the output reading of voltmeter 36 should immediately drop to zero, since timer 54 has interrupted the test current path. Function switch 40 is then returned to the null-potential position 2 and the voltmeter readout should slowly decrease and approach a zero-volt potential, although it may never return exactly to zero volts. To insure accuracy of the reading, the function switch 40 may be cycled through the rest of its positions to verify that voltmeter 36 is still properly calibrated and that all the batteries supplying power to the voltmeter and to the corrosion meter 2 are still within operational limits. The measurement taken may also be further verified by taking a second test measurement, and this may be done with either anodic or cathodic current. In the original test was run in the anodic position of test current reversing switch 48, as illustrated in FIG. 2, the position of switch 48 may be changed to allow the next test run to be with a cathodic current. The direction of test current should have substantially no effect on the corrosion current reading obtained with corrosion meter 2.

The operation of corrosion meter 2 is based upon the linear polarization equation which has been described as follows:

$$\frac{\Delta E}{\Delta i_{app}} = \frac{B_a B_c}{2.3 (i_{corr})(B_a + B_c)} \quad (1)$$

where $\Delta E$ is the change in potential in volts of a metal specimen caused by the application of a polarizing current $\Delta i_{app}$ in amperes; $i_{corr}$ is the corrosion current is amperes, and $B_a$ and $B_c$ are the anodic and cathodic Tafel slopes which can be derived from a complete E log I plot. In most cases, it can be assumed that $B_a = B_c$, reducing equation (1) to:

$$\frac{\Delta E}{\Delta i_{app}} = \frac{B_c}{4.6 (i_{corr})} \quad (2)$$

In addition, the range of Tafel slopes is 0.5 to 0.15 for most corrosion systems, and the value 0.12 is often used for approximations. Assuming the $B_c = 0.12$, equation (2) can be further reduced to:

$$\frac{\Delta E}{\Delta i_{app}} = \frac{0.026}{i_{corr}} \quad (3)$$

Since the corrosion current is the quantity being sought, the equation (3) may be rearranged as follows:

$$i_{corr} = 0.026 \left(\frac{\Delta i_{app}}{\Delta E}\right) \quad (4)$$

In the preferred embodiment, a fixed $\Delta E$ of 10 mv was selected, and for this value equation (4) reduces to:

$$i_{corr} = 2.6 \, \Delta i_{app} \quad (5)$$

It is from this final equation that the resistor values which are switched in series with the test current by corrosion-current range switch 50 of FIG. 2 were selected. By use of these precisely selected resistors, the test current is not only converted to a voltage which the voltmeter 36 can read, but the proper multiplication factor is included for converting test current into corrosion current.

It is apparent that the presumed values used for reducing the linear polarization equation (1) to the simple form of equation (5) are not accurate for all well casings, even though they are good in most cases. Even where the $B_a$ and $B_c$ values differ substantially from the presumed value, a given value is normally valid for all wells within a given geological formation. The corrosion-current reading taken from a given well in a new area may therefore be compared to a downhold log or an E log I plot to determine the accuracy of the corrosion-current readings. If a significant difference is detected, a correction factor is calculated from one or more comparisons, and that factor is then applied to corrosion-current readings taken on the rest of the wells within the same area.

It is also apparent that the circuitry shown in FIGS. 2 and 3 may be modified greatly within the scope of this invention. For example, if the digital readout and accuracy of digital voltmeter 36 are not required, it could be replaced with a panel meter. It is also possible to place current-detecting resistors of various values on plug-in boards to allow field changing of the multiplication factor where it is determined that the Tafel slopes differ from the presumed value. Additionally, the current generator of FIG. 3 could be replaced with an operational amplifier current source having an input for detecting a 10 mv change in the well casing to reference electrode potential and an output for supplying the current required to maintain the 10 mv change. This arrangement would eliminate the continued readjustment of test-current adjustment potentiometer 52 and would additionally make the test current independent of the current detection resistors. Other changes and modifications may be made in the apparatus described in this detailed specification within the spirit and scope of the present invention as defined in the appended claims.

I claim:

1. Apparatus for measuring the external corrosion current of a well casing comprising:
   a voltmeter coupled to said well casing,
   a reference electrode in contact with the earth and coupled to said voltmeter for providing a reference voltage to allow detection of changes in the well casing to earth potential,
   a variable current source coupled to the earth and to said well casing for supplying a test current to the casing to earth circuit to cause a preselected voltage change in the casing to earth potential of less than about 0.020 volt, and
   current detecting means for detecting the test current supplied to said casing to earth circuit by said current source, whereby said corrosion current is proportional to the ratio of said current to said voltage change. a 2. Corrosion current measuring apparatus according to claim 1 wherein said voltmeter is a electronic digital voltmeter.

3. Corrosion current measuring apparatus according to claim 1 wherein said reference electrode is a copper/copper sulfate electrode comprising a vertical insulating cylinder, a porous plug closing the lower end of said cylinder, a saturated copper sulfate solution within said cylinder and permeating said porous plug, and a copper rod within said cylinder and in contact with said copper sulfate solution.

4. Corrosion current measuring apparatus according to claim 1 wherein said variable current source comprises a voltage regulator having a variable output voltage level.

5. Corrosion current measuring apparatus according to claim 4 wherein said voltage regulator includes a manually adjustable variable resistor and said output voltage is proportional to the setting of said variable resistor.

6. Corrosion current measuring apparatus according to claim 1 wherein said current detecting means is a resistor connected in series with the test current path, and coupled to said voltmeter for providing a voltage proportional to said test current to said voltmeter.

7. Corrosion current measuring apparatus according to claim 6 wherein said resistor has a resistance value in ohms equal to the ratio of corrosion current to test current for a preselected change of well casing to earth potential.

8. Corrosion current measuring apparatus according to claim 7 wherein said resistor has a resistance value of 2.6 ohms.

9. A method for measuring the external corrosion current of a well casing comprising:
supplying a current to the casing to earth circuit by means of a ground electrode in contact with the earth, said current having a level selected to cause a casing to earth voltage change of less than about 0.020 volts, and
measuring said current and said well casing to earth voltage change,
whereby the ratio of said current to said voltage change is proportional to the external corrosion current.

* * * * *

UNITED STATES PATENT OFFICE
CERTIFICATE OF CORRECTION

PATENT NO. : 3,999,121
DATED : December 21, 1976
INVENTOR(S) : John M. Taylor, Jr., It is certified that error appears in the above-identified patent and that said Letters Patent are hereby corrected as shown below:

Column 1, line 54, "the" (first Occurence) should read --that--.

Column 2, line 43 "10 my" should read --10 mv--.

Column 4, line 52, after "throw" and before "44" insert --switch--.

Column 5, line 33, "19" should read --10--; line 39 after "flowing" and before "resistor" insert --through--.

Column 6, line 30 "FIGS" should read --FIGURE--.

Column 7, line 43, "is" (second occurrence) should read --in--.

Column 8, line 22 "downhold" should read --downhole--.

Claim 1, column 8, line 68, delete "a".

Signed and Sealed this

Twenty-second Day of March 1977

[SEAL]

Attest:

RUTH C. MASON
Attesting Officer

C. MARSHALL DANN
Commissioner of Patents and Trademarks